United States Patent
Yu et al.

(10) Patent No.: US 8,834,692 B2
(45) Date of Patent: Sep. 16, 2014

(54) DISSOLVED OXYGEN MEASUREMENT SYSTEM

(75) Inventors: Han Young Yu, Daejeon (KR); Yark Yeon Kim, Daejeon (KR); Yong Ju Yun, Daejeon (KR); Won Ick Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 584 days.

(21) Appl. No.: 13/218,830

(22) Filed: Aug. 26, 2011

(65) Prior Publication Data

US 2012/0125768 A1    May 24, 2012

(30) Foreign Application Priority Data

Nov. 22, 2010    (KR) .................. 10-2010-0116321

(51) Int. Cl.
*G01N 27/26* (2006.01)
*G01N 27/30* (2006.01)
*G01N 27/407* (2006.01)

(52) U.S. Cl.
CPC .................. *G01N 27/407* (2013.01)
USPC ...................... 204/406; 205/285.5

(58) Field of Classification Search
CPC .... G01N 27/27; G01N 27/407; G01N 27/409
USPC ........................ 204/406; 205/785.5
See application file for complete search history.

(56) References Cited

U.S. PATENT DOCUMENTS 3,196,100 A * 7/1965 Digby .................. 204/415
2012/0073982 A1 * 3/2012 Lambie .................. 205/343

FOREIGN PATENT DOCUMENTS

| KR | 1020020066905 A | 8/2002 |
| KR | 10-0356342 B1 | 10/2002 |
| KR | 1020040037747 A | 5/2004 |
| KR | 10-0483584 B1 | 4/2005 |

* cited by examiner

*Primary Examiner* — Nicholas A Smith

(57) ABSTRACT

Provided is a dissolved oxygen measurement system. The dissolved oxygen measurement system includes a hydrogen storage device storing hydrogen, a first hydrogen fuel cell in which the hydrogen stored in the hydrogen storage device and water supplied from the outside in real time react with each other to generate first electricity energy, a water storage tank storing the water supplied from the outside, a second hydrogen fuel cell in which the water supplied from the water storage tank and the hydrogen stored in the hydrogen storage device react with each other to generate second electricity energy, and a control unit analyzing a difference between the first electricity energy and the second electricity energy.

10 Claims, 5 Drawing Sheets

DISSOLVED OXYGEN MEASUREMENT SYSTEM

CROSS-REFERENCE TO RELATED APPLICATIONS

This U.S. non-provisional patent application claims priority under 35 U.S.C. §119 of Korean Patent Application No. 10-2010-0116321, filed on Nov. 22, 2010, the entire contents of which are hereby incorporated by reference.

BACKGROUND OF THE INVENTION

The present invention disclosed herein relates to a dissolved oxygen measurement system, and more particularly, a dissolved oxygen measurement system, which measures dissolved oxygen in real-time using hydrogen generated using solar energy as an energy source.

The dissolved oxygen (DO) is the amount of oxygen that is dissolved in water, i.e., the amount of oxygen directly necessary for organisms that live in the water such as fishes and widely used as an indication of the quality of water.

The dissolved oxygen is influenced by a water temperature and the amount of microorganisms. Specifically, when microorganisms are introduced, oxygen is consumed by aerobic microorganisms to reduce the amount of oxygen dissolved in water (dissolved oxygen). Thus, the more the amount of microorganisms within water increases, the more consumption of oxygen is significantly increased. As a result, the amount of oxygen necessary for organisms living in the water may be significantly reduced to deteriorate the quality of water. Accordingly, the measurement of the amount of microorganisms can prevent a river from being contaminated. However, since it is difficult to directly measure the total microorganisms, oxygen within water taken from a river is measured, and then, oxygen consumed by microorganisms as time goes on is measured to predict some how many microorganisms there are.

For example, a method of measuring the amount of oxygen dissolved in water (dissolved oxygen) may include an electrochemical measurement method and a method using a pressure variation due to consumption of oxygen.

The method of electrochemically measuring a concentration of oxygen is a method in which a concentration of oxygen measured through electrochemical current is reduced when the amount of oxygen consumed by microorganisms is increased. This method may detect the oxygen concentration from the amount of current flowing through three electrodes that is used in a general cyclic voltammetry method. Also, according to the electrochemical measurement method, the amount of oxygen is analyzed by transmitting only oxygen and blocking liquid using a membrane through which only oxygen is filtered.

On the other hand, according to the method using the pressure variation, oxygen that can maintain a certain oxygen pressure is injected into water, and then, pressure reduction of oxygen is measured using a pressure sensor because the amount of initially injected oxygen is reduced according to the amount of oxygen consumed by microorganisms in water.

As described above, in the methods of measuring the oxygen concentration, the predetermined amount of water to be measured in a laboratory is taken to measure the amount of oxygen. Then, the taking water is cultivated in shady facility for about five days to measure again the amount of oxygen. Thereafter, biochemical oxygen demand (BOD) is determined by the difference between the amounts of oxygen measured in the two samples. However, in these oxygen concentration measurement methods, it is impossible to measure the dissolved oxygen in real time. That is, since taking water should be cultivated in a laboratory for about five days, it is impossible to measure the dissolved oxygen required to be quickly analyzed.

SUMMARY OF THE INVENTION

The present invention provides a dissolved oxygen measurement system, which is directly installed in a river to measure dissolved oxygen in real time without taking water.

The feature of the present invention is not limited to the aforesaid, but other features not described herein will be clearly understood by those skilled in the art from descriptions below.

Embodiments of the present invention provide dissolved oxygen measurement systems comprising: a hydrogen storage device storing hydrogen; a first hydrogen fuel cell in which the hydrogen stored in the hydrogen storage device and water supplied from the outside in real time react with each other to generate first electricity energy; a water storage tank storing the water supplied from the outside; a second hydrogen fuel cell in which the water supplied from the water storage tank and the hydrogen stored in the hydrogen storage device react with each other to generate second electricity energy; and a control unit analyzing a difference between the first electricity energy and the second electricity energy.

Other features and aspects will be apparent from the following detailed description, the drawings, and the claims.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
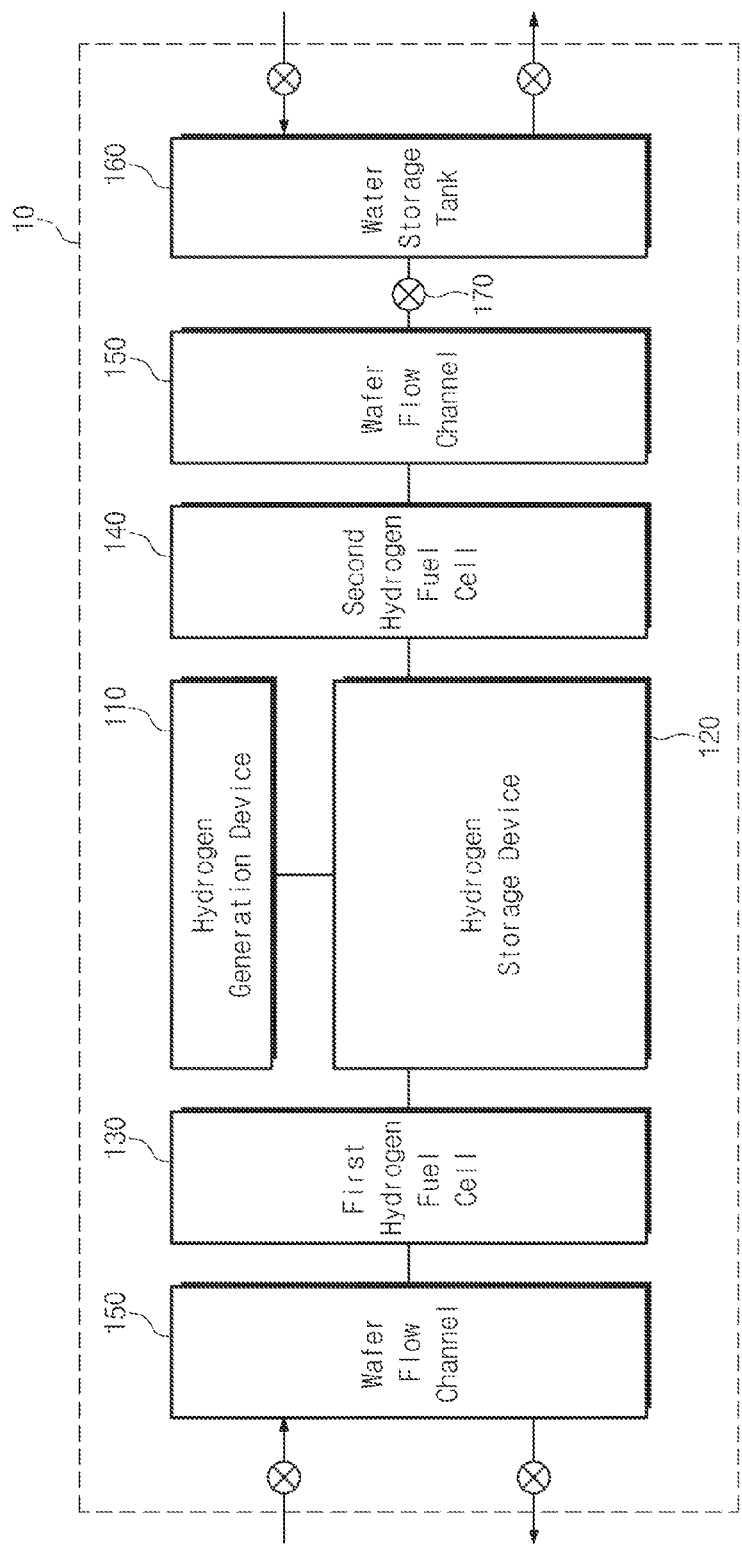
FIG. 1 is a block diagram of a dissolved oxygen measurement apparatus according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explain a specific exemplary embodiment while not limiting the present invention. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components.

According to an embodiment, a dissolved oxygen measurement system includes a first measurement unit measuring dissolved oxygen in water supplied from a river in real time, a river water storage unit storing the water supplied from the river, a second measurement unit measuring the dissolved oxygen in the water stored in the river water storage unit, and a control unit analyzing a difference between the dissolved oxygen measured by the first measurement unit and the dissolved oxygen measured by the second measurement unit.

Hereinafter, a dissolved oxygen measurement apparatus according to an embodiment of the present invention will be described with reference to the accompanying drawings.

FIG. 1 is a block diagram of a dissolved oxygen measurement apparatus according to an embodiment of the present invention.

Figure 2:
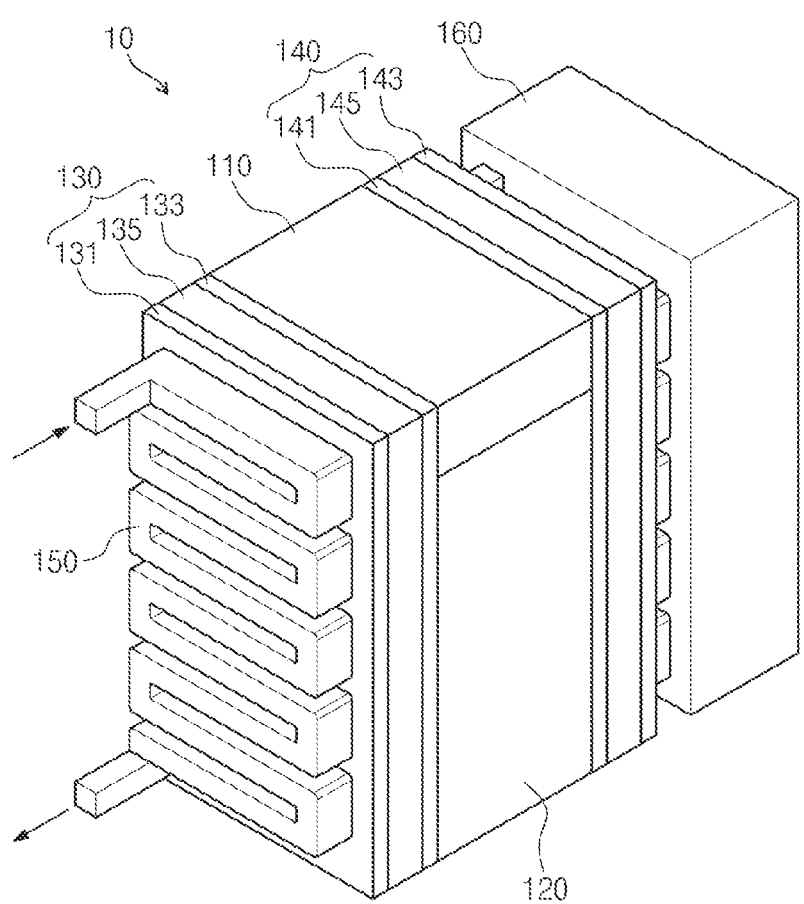
FIG. 2 is a schematic perspective view of a dissolved oxygen measurement apparatus according to an embodiment of the present invention.

FIG. 2 is a schematic perspective view of a dissolved oxygen measurement apparatus according to an embodiment of the present invention.

Referring to FIGS. 1 and 2, a dissolved oxygen measurement apparatus 10 according to an embodiment includes a hydrogen generation device 110, a hydrogen storage device 120, and first and second hydrogen fuel cells 130 and 140. Furthermore, the dissolved oxygen measurement apparatus 10 includes a water flow channel 150 supplying water from a river to the first hydrogen fuel cell 130 in real time. The amount and supply time of water supplied into the first hydrogen fuel cell 130 may be adjusted according to a length of the wafer flow channel 150. Also, the dissolved oxygen measurement apparatus 10 includes a wafer storage tank 160 storing the water taken from the river. The water stored in the water storage tank 160 is supplied into the second hydrogen fuel cell 140. Furthermore, the water flow channel 150 may be disposed between the second hydrogen fuel cell 140 and the water storage tank 160.

According to an embodiment, as shown in FIG. 2, the first hydrogen fuel cell 130 may be disposed between the water flow channel 150 and the hydrogen storage device 120, and the second hydrogen fuel cell 140 may be disposed between the second hydrogen fuel cell 140 and the hydrogen storage device 120. Also, according to an embodiment, a control valve 170 controlling the amount and supply time of water supplied from the water storage tank 160 to the second hydrogen fuel cell 140 may be disposed between the water storage tank 160 and the second hydrogen fuel cell 140. The amount of water stored in the water storage tank 160 may be controlled by opening/closing the control valve 170. That is, the control valve 170 may be opened or closed at each desired time to be measured to measure the dissolved oxygen, thereby measuring a variation in the dissolved oxygen.

The dissolved oxygen measurement apparatus 10 may be directly installed in each of rivers spread across the nation. Thus, water in which microorganisms exist may be supplied into the first hydrogen fuel cell 130 through the water flow channel 150 in real time. Also, the water supplied from the river and containing the microorganisms may be stored in the water storage tank 160. As time goes by, oxygen stored in the water storage tank 160 may be consumed by microorganisms to reduce the amount of oxygen. That is, with the passage of time, the dissolved oxygen in the water supplied into the second hydrogen fuel cell 140 may be less than that of the water supplied into the first hydrogen fuel cell 130. Also, an actual biochemical oxygen demand (BOD) may be decided by a difference between the amounts of oxygen obtained from the first and second hydrogen fuel cells 130 and 140. A method of measuring the dissolved oxygen in the first and second hydrogen fuel cells 130 and 140 will be described later with reference to FIGS. 2 and 4.

Figure 3:
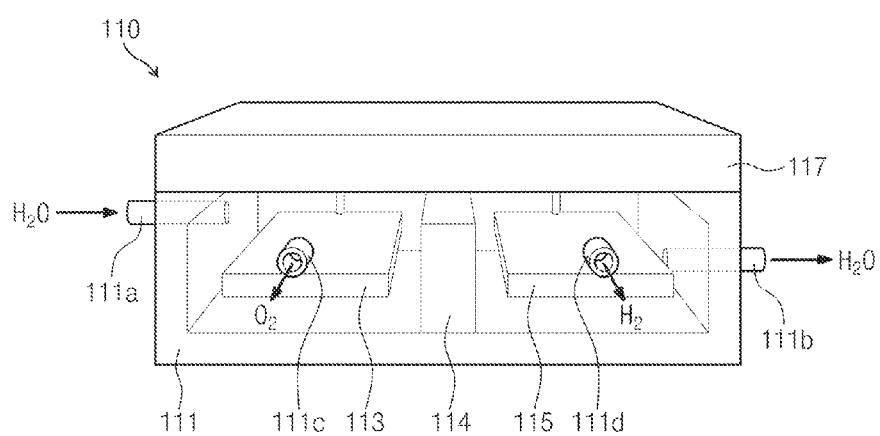
FIG. 3 is a view of a hydrogen generating device included in a dissolved oxygen measurement apparatus according to an embodiment of the present invention.

FIG. 3 is a view of a hydrogen generating device included in a dissolved oxygen measurement apparatus according to an embodiment of the present invention;

According to an embodiment, the hydrogen generation apparatus 10 may be driven by electricity energy generated using solar light. The hydrogen generation apparatus 10 may electrolyze the water taken from the river to generate hydrogen. The hydrogen generated in the hydrogen generation apparatus 10 may be stably stored in the hydrogen storage device 20 through a physical or chemical storage method. Here, the hydrogen may be stored in a gas state or absorbed onto a hydrogen storage medium. When the hydrogen is absorbed onto the hydrogen storage medium, the hydrogen may be absorbed onto the hydrogen storage medium through physical bonding and chemical bonding. Here, a heating device (not shown) may be provided to discharge hydrogen from the hydrogen absorbed through the physical and chemical bonding. To discharge the hydrogen from the hydrogen absorbed through the physical and chemical bonding to the outside, the heating device supplies thermal energy to increase thermal energy of the hydrogen, thereby separating the hydrogen from the hydrogen storage medium.

Referring to FIG. 3, the hydrogen generation device 110 includes a chamber 111, positive and negative electrodes 113 and 115, and a power source 117 applying a power to the electrodes 113 and 115.

An inflow port 111a through which water is introduced from a river and a discharge port 111b through which electrolyzed water is discharged are disposed in the chamber 111. The chamber 111 may be divided into a negative electrode chamber and a positive electrode chamber by a membrane. The positive electrode 113 is disposed within the positive electrode chamber, and the negative electrode 115 is disposed within the negative electrode chamber 115. Gas discharge tubes 111c and 111d for discharging oxygen gas and hydrogen gas generated by electrolysis may be disposed in the positive and negative electrode chambers, respectively.

The membrane dividing the chamber 111 may be a proton exchange membrane (PEM). Alternatively, an inorganic membrane, asbestos, or special porous diaphragm may be used as the membrane.

A predetermined voltage may be applied from the power source 117 to the positive and negative electrodes 113 and 115. According to an embodiment, the positive and negative electrodes 113 and 115 may be connected to a power source electrode of a solar cell. A precious metal such as platinum, nickel, cobalt, or copper may be used as the positive and negative electrodes 113 and 115.

In an embodiment, the power source 117 may be the solar cell. The solar cell is a device that directly converts solar light into electricity using a photovoltaic effect in which the solar light is incident into a semiconductor diode having a p-n junction to generate electrons. The solar cell may include one of a dye sensitized solar cell, a silicon solar cell, a compound semiconductor solar cell, and a stacked solar cell. The solar cell may apply a predetermined voltage to both ends of the electrodes 113 and 115 disposed within the chamber 111.

In the hydrogen generation device 110, when a voltage is applied from the solar cell to the positive and negative electrodes 113 and 115, the water introduced into the chamber 111 may be electrolyzed into oxygen ($O_2$), electrons (e—), and hydrogen ions (H+/proton). The hydrogen ions are dissolved into the water and moved into the negative electrode 115 through the membrane 114. Also, the electrons are moved from the positive electrode 113 to the negative electrode 115 through the solar cell. Thus, the electrons and the hydrogen ions may react with each other in the negative electrode 115 to generate the hydrogen gas. That is, the hydrogen may be generated in the negative electrode chamber of the hydrogen generation device 110. The oxygen may be generated in the positive electrode chamber. The hydrogen generated in the negative electrode chamber may be stored in the hydrogen storage device (see reference numeral 120 of FIG. 2) through the gas discharge tube 111d, and the oxygen generated in the positive electrode chamber may be discharged to the outside through the gas discharge tube 111c.

Figure 4:
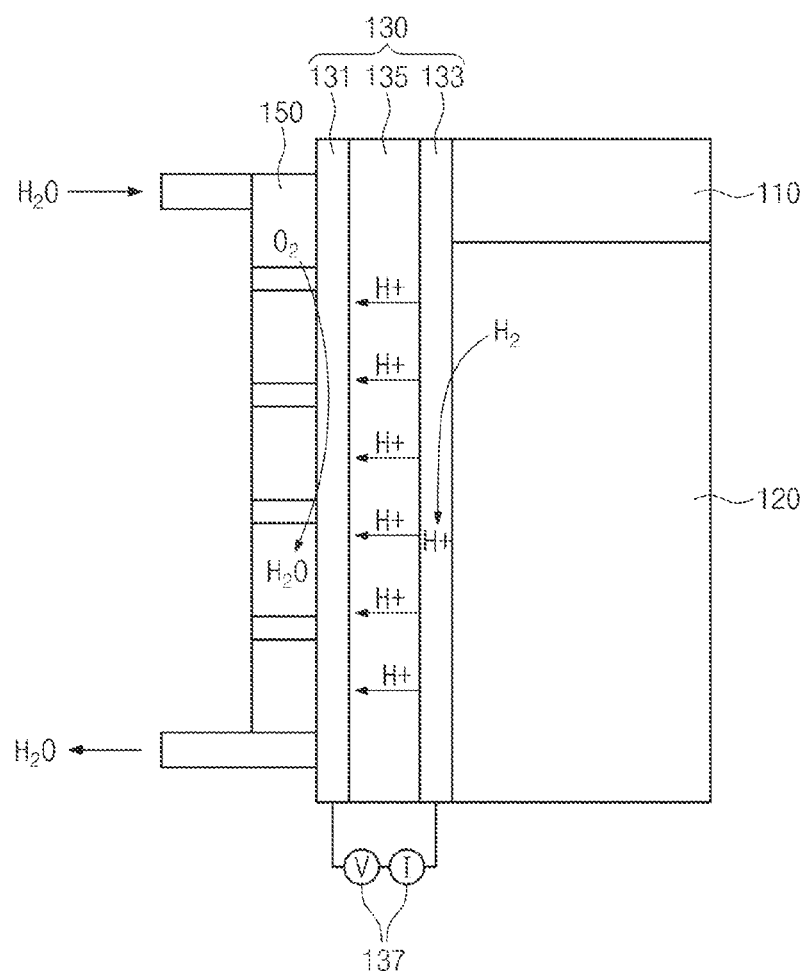
FIG. 4 is a view of a first hydrogen fuel cell included in a dissolved oxygen measurement apparatus according to an embodiment of the present invention.

FIG. 4 is a view of a first hydrogen fuel cell included in a dissolved oxygen measurement apparatus according to an embodiment of the present invention; and According to an embodiment, the first and second hydrogen fuel cells (see reference numerals 130 and 140 of FIG. 2) convert chemical energy generated when the hydrogen gas supplied from the hydrogen storage device 120 reacts with the oxygen of the water taken from the river into electrical energy. In an embodiment, the amount of oxygen existing in the water supplied from the river in real time may be measured by the first hydrogen fuel cell 130, and the amount of oxygen consumed by the microorganisms existing in the water taken from the river may be measured by the second hydrogen fuel cell 140.

As shown in FIG. 4, the first hydrogen fuel cell (see reference numeral 130 of FIG. 2) includes a cathode 131, an anode 133, a hydrogen ion exchange membrane 135, and an electrical signal measurement unit 137 (i.e., external circuit). Here, a noble metal such as platinum and nickel, cobalt, or copper may be used as the cathode 131 and the anode 133. The first and second hydrogen fuel cells (see reference numerals 130 and 140 of FIG. 2) may include an inflow port (not shown) for transferring hydrogen gas to the anode 133 and an inflow port (not shown) for transferring oxygen gas to the cathode 131. Similarly, the second hydrogen fuel cell (see reference numeral 140 of FIG. 2) may have the same components as the first hydrogen fuel cell (see reference numeral 130 of FIG. 2). The hydrogen gas supplied into the anode 133 is decomposed into hydrogen ions and electrons by a catalyst. The hydrogen ions are moved into the cathode 131 through the hydrogen ion exchange membrane 135. The hydrogen ions may be bonded to the oxygen existing in the water supplied from the water flow channel 150 to the cathode 131 to generate new water in the cathode 131. That is, the hydrogen gas is oxidized in the anode 133 by the catalyst to generate the hydrogen ions. Then, the hydrogen ions pass through the hydrogen ion exchange membrane 135 to react with the oxygen in the cathode 131 and are deoxidized.

The electrons generated in the anode 133 does not pass through the hydrogen ion exchange membrane 135 and are moved into the cathode 131 through the electrical signal measurement unit 137 (i.e., the external circuit). When the electrons are moved into the cathode 131 through the electrical signal measurement unit 137 (i.e., the external circuit), a current is generated. This may be measured in the electrical signal measurement unit 137 such as an ammeter and/or a voltameter. That is to say, the movement of the hydrogen ions from the anode 133 to the cathode 131 may be outputted as a current or voltage variation in the electrical signal measurement unit 137. When the water supplied from the river and the hydrogen ions react with each other, the current or voltage measured in the electrical signal measurement unit 137 are varied according to the amount of oxygen (i.e., dissolved oxygen) in the water. Thus, the first hydrogen fuel cell 130 may measure the dissolve oxygen in the introduced water in a real time. Also, the second hydrogen fuel cell 140 may measure the amount of oxygen consumed by the microorganisms because the water supplied from the river is stored in the water storage tank 160 for a predetermined time. Furthermore, since the second hydrogen fuel cell 160 measures the reduced amount of oxygen, current and voltage measured in the second hydrogen fuel cell 140 may be less than those measured in the first hydrogen fuel cell 130. Thus, as a difference between the amounts of oxygen measured in the first and second hydrogen fuel cells 130 and 140 is analyzed, the actual BOD can be obtained.

In more detail, reference to FIGS. 2 and 4, the hydrogen gas may be supplied from the hydrogen storage device 120 into the anode 133 of the first hydrogen fuel cell 130. The water introduced into the river may be continuously supplied into the cathode 131 of the first hydrogen fuel cell 130 through the water flow channel 150 in real time. Here, the electrical signal measurement unit 137 of the first hydrogen fuel cell 130 is connected between the anode 133 and the cathode 131 to measure an electrical signal generated when the oxygen existing in the water supplied from the river in real time and the hydrogen ions react with each other. That is, since the water is supplied from the river into the first hydrogen fuel cell 130, the dissolved oxygen may be measured in real time.

Referring to FIG. 2, the hydrogen gas may be supplied from the hydrogen storage device 120 into the anode 143 of the second hydrogen fuel cell 140. Also, the water may be supplied from the water storage tank 160 to the cathode 141. The water flow channel 150 may be disposed between the water storage tank 160 and the second hydrogen fuel cell 140 to continuously supply the water. Furthermore, the control valve (see reference numeral 170 of FIG. 1) may be disposed between the water storage tank 160 and the water flow channel 150 connected to the second hydrogen fuel cell 140 to control the supply of the water stored in the water storage tank 160. The water stored in the water storage tank 160 may be continuously or periodically supplied into the second hydrogen fuel cell 140 by the control valve (see reference numeral 170 of FIG. 1). That is, the second hydrogen fuel cell 140 may measure the dissolved oxygen at each of desired times.

The electrical signal measurement unit of the second hydrogen fuel cell 140 may be connected between the anode 143 and the cathode 141, like the first hydrogen fuel cell 130 illustrated in FIG. 4. Thus, the electrical signal measurement unit measures an electrical signal generated when oxygen existing in the water in which the oxygen is consumed by microorganisms and the hydrogen ions react with each other.

Since aerobic microorganisms exist in the water supplied from the river and stored in the water storage tank 160, oxygen in the water stored in the water storage tank 160 may be consumed by the aerobic microorganisms as time goes by. Thus, to analyze the amount of microorganisms existing in the river, the water stored in the water storage tank 160 may be supplied into the second hydrogen fuel cell 140 through the control valve (see reference numeral 170 of FIG. 1) after a predetermined time elapses. Here, the water supply time and flowrate may be controlled by the control valve (see reference numeral 170 of FIG. 1).

Since the water supplied from the water storage tank 160 to the second hydrogen fuel cell 140 is consumed by the microorganisms, the amount of oxygen in the water supplied from the water storage tank 160 to the second hydrogen fuel cell 140 is less than that in the water supplied from the river to the first hydrogen fuel cell 130 in real time. That is, since water in which a predetermined time elapses after being supplied from the river is supplied to the second hydrogen fuel cell 140, a variation with respect to an initial value may be measured. Furthermore, since the water supply time may be controlled in the second hydrogen fuel cell 140 through the control valve 170, the dissolved oxygen may be measured in real time. That is, the dissolved oxygen measurement apparatus 10 according to an embodiment may measure the amount of oxygen consumed by the microorganisms in real time.

Figure 5:
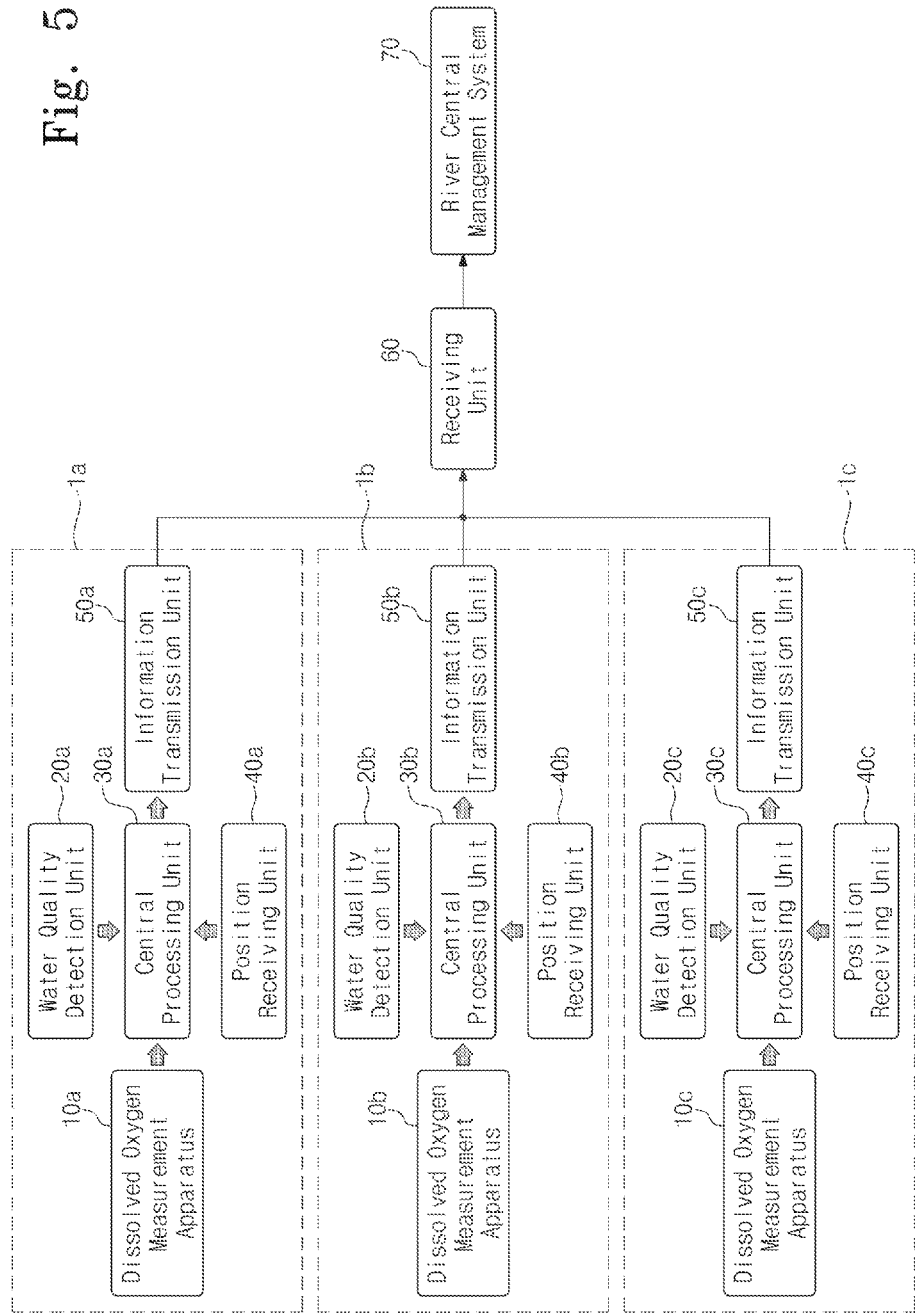
FIG. 5 is a conceptual view of a dissolved oxygen measurement system including a dissolved oxygen measurement apparatus according to an embodiment of the present invention.

As described above, the electrical signals measured in the first and second hydrogen fuel cells (see reference numerals 130 and 140 of FIG. 2) of the dissolved oxygen measurement apparatus 10, as shown in FIG. 5, may be transmitted into a central processing unit (see reference numerals 30a, 30b, and 30c of FIG. 5) to analyze a difference of the dissolved oxygen. Here, the difference of the dissolved oxygen (i.e., a difference between the electrical signals measured in the first and second hydrogen fuel cells 130 and 140) may be in proportion to the amount of microorganisms existing in the river. That is, the more the amount of microorganisms existing in the river is decreased, the more the difference between the electrical signals measured in the first and second hydrogen fuel cells 130 and 140 may be decreased. Also, the more the amount of microorganisms existing in the river is increased, the more the difference between the electrical signals measured in the first and second hydrogen fuel cells 130 and 140 may be increased. That is to say, when the difference between the electrical signal measured in the first hydrogen fuel cell 130 and the electrical signal measured in the second hydrogen fuel cell 140 is large, it is seen that the amount of microorganisms existing in the water taken from the river is large. Thus, water quality of the river may be grasped based on the above-described principle. Therefore, the difference between the electrical signals measured in the first and second hydrogen fuel cells (see reference numerals 130 and 140 of FIG. 2) may be analyzed to predict the amount of microorganisms existing in the river, thereby managing the water quality of the river.

FIG. 5 is a conceptual view of a dissolved oxygen measurement system including a dissolved oxygen measurement apparatus according to an embodiment of the present invention.

According to an embodiment, a river management system includes dissolved oxygen measurement systems 1a, 1b, and 1c respectively installed in rivers spread across the nation, a receiving unit 60 for receiving data measured by the dissolved oxygen measurement systems 1a, 1b, and 1c, and a river central management system 70 for analyzing and managing the dissolved oxygen measured by the dissolved oxygen measurement systems 1a, 1b, and 1c.

As shown in FIG. 5, the dissolved oxygen measurement systems 1a, 1b, and 1c respectively installed in the rivers spread across the nation includes dissolved oxygen measurement apparatuses 10a, 10b, and 10c, water quality detection units 20a, 20b, and 20c, central processing units 30a, 30b, and 30c, and position receiving units 40a, 40b, and 40c, and information transmission units 50a, 50b, and 50c. The dissolved oxygen measurement systems 1a, 1b, and 1c may be installed in the rivers spread across the nation, respectively.

The water quality detection units 20a, 20b, and 20c detect information obtained by analyzing the amounts of phosphor and nitrogen existing in the rivers in addition to the dissolved oxygen in the rivers.

The central processing units 30a, 30b, and 30c process data transmitted from each of the dissolved oxygen measurement apparatuses 10a, 10b, and 10c, the water quality detection units 20a, 20b, and 20c, and the position receiving units 40a, 40b, and 40c. That is, the central processing units 30a, 30b, and 30c compile, compare, and analyze data with respect to the amount of oxygen and other water quality data.

The position receiving units 40a, 40b, and 40c receive each position information of the dissolved oxygen measurement apparatuses 10a, 10b, and 10c using a global positioning system (GPS).

The information transmission units 50a, 50b, and 50c transmit data processed by the central processing units 30a, 30b, and 30c to the receiving unit 60 connected to the river central management system 70. The river central management system 70 analyzes the dissolved oxygen measured by the dissolved oxygen measurement systems 1a, 1b, and 1c and manages the water quality of the rivers according to the analyzed results.

According to the dissolved oxygen measurement system, since the dissolved oxygen measurement apparatus is directly installed in the river, it may be unnecessary to take the water from the river and cultivate the taken water in a laboratory to measure the dissolved oxygen. That is, manpower and time required for measuring the dissolved oxygen may be reduced. Also, since the dissolved oxygen measurement apparatus directly installed in the river uses the solar light as an energy source, the dissolved oxygen measurement apparatus may be used semipermanently. Furthermore, the dissolved oxygen measurement apparatuses may be respectively installed in the rivers spread across the nation and data transmitted from the dissolved oxygen measurement apparatuses may be compiled, compared, and analyzed to compare the rivers spread across the nation to each other and manage the rivers spread across the nation. Also, since the dissolved oxygen measurement apparatuses utilize electricity energy obtained from solar as an energy source, it is unnecessary to supply and manage additional energy. That is, since the solar cell generating hydrogen in the dissolved oxygen measurement apparatus includes a secondary battery (not shown) that is an auxiliary energy storage device, the storage and management of power may be easily performed.

According to the embodiments of the present invention, since the dissolved oxygen measurement apparatus is directly installed in the river, the dissolved oxygen may be quickly and continuously analyzed without taking water.

According to the embodiments of the present invention, the data of the dissolved oxygen directly measured in the river may be transmitted into the central processing unit to analyze the quality of water together with other water quality analysis data in addition to the dissolved oxygen.

Also, according to the embodiments of the present invention, it may be easy to compare and analyze qualities of water in the rivers spread across the nation.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A dissolved oxygen measurement system comprising:
a hydrogen storage device storing hydrogen;
a first hydrogen fuel cell in which the hydrogen stored in the hydrogen storage device and water supplied from the outside in real time react with each other to generate first electricity energy;
a water storage tank storing the water supplied from the outside;
a second hydrogen fuel cell in which the water supplied from the water storage tank and the hydrogen stored in the hydrogen storage device react with each other to generate second electricity energy; and
a control unit analyzing a difference between the first electricity energy and the second electricity energy.

2. The dissolved oxygen measurement system of claim 1, further comprising a hydrogen generation device electrolyzing the water supplied from the outside using electricity energy generated from solar light to generate hydrogen.

3. The dissolved oxygen measurement system of claim 2, wherein the system is operated by the electricity energy generated from the solar light.

4. The dissolved oxygen measurement system of claim 2, wherein the hydrogen generation device comprises:
a chamber storing the water supplied from the outside;
positive and negative electrodes disposed within the chamber;
a hydrogen ion exchange membrane disposed between the positive and negative electrodes in the chamber; and
a solar cell disposed outside the chamber, the solar cell being connected to the positive and negative electrodes.

5. The dissolved oxygen measurement system of claim 1, wherein the first hydrogen fuel cell comprises an anode, a cathode, a hydrogen ion exchange membrane disposed between the anode and the cathode, and an external circuit electrically connecting the anode to the cathode,
wherein the hydrogen is supplied into the cathode and the water is supplied into the anode from the outside in real time.

6. The dissolved oxygen measurement system of claim 5, wherein the external circuit comprises an ammeter and/or a voltameter, which measure(s) the first electricity energy.

7. The dissolved oxygen measurement system of claim 5, further comprising a water flow channel continuously supplying the water into the anode of the first hydrogen fuel cell from the outside.

8. The dissolved oxygen measurement system of claim 1, wherein the second hydrogen fuel cell comprises an anode, a cathode, a hydrogen ion exchange membrane disposed between the anode and the cathode, and an external circuit connecting the anode to the cathode,
wherein the hydrogen is supplied into the cathode and the water stored in the water storage tank is supplied into the anode.

9. The dissolved oxygen measurement system of claim 8, wherein the external circuit comprises an ammeter and/or a voltameter, which measure(s) the second electricity energy.

10. The dissolved oxygen measurement system of claim 8, further comprising a control valve controlling a flowrate and supply time of the water supplied into the anode of the second hydrogen fuel cell from the water storage tank.

* * * * *